(12) United States Patent
Lee et al.

(10) Patent No.: US 12,251,334 B2
(45) Date of Patent: Mar. 18, 2025

(54) SKIN MANAGEMENT DEVICE

(71) Applicant: APR CO., LTD., Seoul (KR)

(72) Inventors: Jeong Ho Lee, Seoul (KR); Do Hee Kang, Gangnam-gu (KR)

(73) Assignee: APR CO., LTD., Seoul (KR)

( * ) Notice: Subject to any disclaimer, the term of this patent is extended or adjusted under 35 U.S.C. 154(b) by 0 days.

(21) Appl. No.: 17/907,110

(22) PCT Filed: May 2, 2022

(86) PCT No.: PCT/KR2022/006274
§ 371 (c)(1),
(2) Date: Sep. 23, 2022

(87) PCT Pub. No.: WO2023/113112
PCT Pub. Date: Jun. 22, 2023

(65) Prior Publication Data
US 2024/0245549 A1 Jul. 25, 2024

(30) Foreign Application Priority Data
Dec. 17, 2021 (KR) .................. 10-2021-0182213

(51) Int. Cl.
*A61F 7/00* (2006.01)
*A61N 7/02* (2006.01)
*A61N 7/00* (2006.01)

(52) U.S. Cl.
CPC ............... *A61F 7/007* (2013.01); *A61N 7/02* (2013.01); *A61F 2007/0052* (2013.01); *A61F 2007/0087* (2013.01); *A61N 2007/0034* (2013.01)

(58) Field of Classification Search
CPC .............. A61F 7/007; A61F 2007/0052; A61F 2007/0087; A61N 7/02; A61N 2007/0034
See application file for complete search history.

(56) References Cited

U.S. PATENT DOCUMENTS

| | | | |
|---|---|---|---|
| 7,955,262 B2 | 6/2011 | Rosenberg | |
| 10,376,693 B2 | 8/2019 | Yamazaki | |
| 11,241,591 B2 | 2/2022 | Stoddard et al. | |
| 2007/0038156 A1* | 2/2007 | Rosenberg | A61N 7/02 601/2 |
| 2007/0179482 A1* | 8/2007 | Anderson | A61B 18/203 606/2 |
| 2007/0239075 A1* | 10/2007 | Rosenberg | A61N 1/328 601/2 |

FOREIGN PATENT DOCUMENTS

| | | |
|---|---|---|
| CN | 108992789 | 12/2018 |
| JP | 2002345915 | 12/2002 |
| JP | 2011194175 | 10/2011 |
| JP | 2014168698 | 9/2014 |
| JP | 2016187732 | 11/2016 |
| JP | 2019037687 | 3/2019 |
| KR | 20080074853 | 8/2008 |
| KR | 20170075129 | 7/2017 |
| KR | 20180039678 | 4/2018 |
| KR | 20200069432 | 6/2020 |
| KR | 20200101904 | 8/2020 |

* cited by examiner

*Primary Examiner* — Bo Joseph Peng
(74) *Attorney, Agent, or Firm* — Perman & Green, LLP

(57) ABSTRACT

Disclosed is a skin management device with an improved skin management effect as electric deep-heat by high frequency and heat by ultrasound physical vibration may be simultaneously provided to the skin.

9 Claims, 6 Drawing Sheets

SKIN MANAGEMENT DEVICE

CROSS REFERENCE TO RELATED APPLICATIONS

This application is a National Stage of International Application No. PCT/KR2022/006274, having an International Filing Date of 2 May 2022, which designated the United States of America, and which claims priority from and the benefit of Korean Patent Application No. 10-2021-0182213 filed on 17 Dec. 2021, the disclosures of which are incorporated herein by reference in their entireties.

BACKGROUND

1. Field

The present disclosure relates to a skin management device, and more particularly, to a skin management device with an improved skin management effect as electric deep-heat by high frequency and heat by ultrasound physical vibration may be simultaneously provided to the skin.

2. Brief Description of Related Developments

In order to prevent skin aging, various instruments for massaging the skin have been developed. Recently, various apparatuses for providing a massage effect by using high frequency, low frequency, or ultrasound have been released.

Ultrasound beauty devices have the effects of cleaning of removing dead skin cells or waste products and stimulating the dermis to help blood circulation, by vibrating skin with a frequency higher than an audible frequency. However, the ultrasound beauty device, which provides a vibration of a low frequency compared with a high-frequency beauty device is effective in cleaning the skin but has a demerit of not infiltrating deeply into the dermis layer beneath the epidermis.

The high-frequency beauty device may stimulate the dermis by generating deep-heat by using a frequency higher than the ultrasound beauty device. At this time, wrinkle improvement and skin lifting effects can be obtained by regenerating collagen with deep-heat. The principle of generating heat by using high frequency is the same as the principle of heating water by rotating water molecules in a microwave oven. However, as the skin vibrating effect is less than that of the ultrasound beauty device due to high frequency, the high-frequency beauty device has a demerit in the skin cleaning power.

Accordingly, there is a demand for a skin management device that can solve the above problems and compensate for each of the demerits.

SUMMARY

Provided is a skin management device with an improved skin management effect as electric deep-heat by high frequency and heat by ultrasound physical vibration may be simultaneously provided to the skin.

According to an aspect of the disclosure, a skin management device includes a main body portion having a hand piece structure and including a high-frequency generation module for generating high frequency, an ultrasound generation module for generating ultrasound, and a control module, which are mounted on the main body portion, a skin contact head provided at one position of the main body portion to be capable of contacting user's skin, a high-frequency electrode disposed in the skin contact head and connected to the high-frequency generation module, and an ultrasound electrode disposed in the skin contact head and connected to the ultrasound generation module, wherein the control module controls operations of the high-frequency generation module and the ultrasound generation module, and during operations of the high-frequency generation module and the ultrasound generation module, when the skin contact head contacts the user's skin, high frequency and ultrasound are provided to the user's skin.

According to an embodiment, the high-frequency electrode may be a bipolar RF electrode including a positive pole portion and a negative pole portion, which are apart from each other, and the ultrasound electrode may be disposed between the positive pole portion and the negative pole portion.

According to an embodiment, each of the positive pole portion and the negative pole portion may have a crescent shape having a sunken surface, the positive pole portion and the negative pole portion may be disposed at both side portions of the skin contact head, the positive pole portion and the negative pole portion may be disposed such that the sunken surfaces face each other, and the ultrasound electrode may be disposed at a center of the skin contact head between the sunken surfaces of the positive pole portion and the negative pole portion.

According to an embodiment, the skin contact head may include a cover member covering at least a part of the ultrasound electrode.

According to an embodiment, the cover member may include a window hole that exposes the ultrasound electrode.

According to an embodiment, an area of the window hole may optionally vary.

According to an embodiment, the cover member may have a thickness, the window hole may have a depth, an inner circumferential portion of the window hole may have a slope surface, and a cross-sectional area of the window hole may increase toward outside.

According to an embodiment, the control module may have a first operation mode in which the high-frequency generation module and the ultrasound generation module alternately operate.

According to an embodiment, the control module may have a second operation mode in which at least one of the high-frequency generation module and the ultrasound generation module discontinuously operates.

According to an embodiment, the control module may have a third operation mode in which a frequency of high frequency generated by the high-frequency generation module varies.

According to an embodiment, the control module may have a fourth operation mode in which a frequency of ultrasound generated by the ultrasound generation module varies.

According to a skin management device according to an embodiment of the present disclosure, during simultaneous operations of a high-frequency generation module and an ultrasound generation module, when a skin contact head contacts the user's skin, high frequency generated by the high-frequency generation module and ultrasound generated by the ultrasound generation module may be simultaneously provided to the user's skin through a high-frequency electrode and an ultrasound electrode.

Accordingly, electric deep-heat by high frequency and heat by ultrasound physical vibration may be simultaneously provided to the skin. Accordingly, a skin management effect may be improved.

DETAILED DESCRIPTION

A skin management device may include: a main body portion having a hand piece structure and including a high-frequency generation module for generating high frequency, an ultrasound generation module for generating ultrasound, and a control module, which are mounted on the main body portion; a skin contact head provided at one position of the main body portion to be capable of contacting user's skin; a high-frequency electrode disposed in the skin contact head and connected to the high-frequency generation module; and an ultrasound electrode disposed in the skin contact head and connected to the ultrasound generation module, wherein the control module controls operations of the high-frequency generation module and the ultrasound generation module, and, during operations of the high-frequency generation module and the ultrasound generation module, when the skin contact head contacts the user's skin, high frequency and ultrasound are provided to the user's skin.

Hereinafter, the disclosure will be described more fully with reference to the accompanying drawings.

Figure 1:
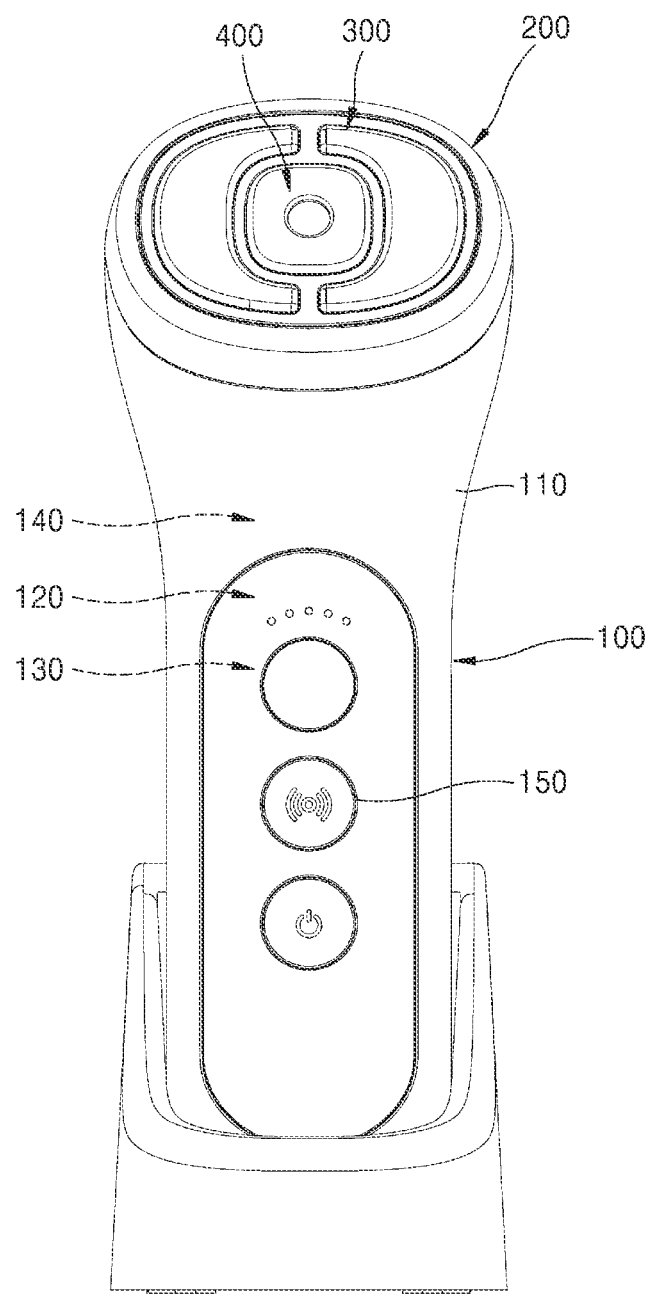
FIGS. 1 and 2 are views showing the appearance of a skin management device according to an embodiment of the present disclosure.
Figure 2:
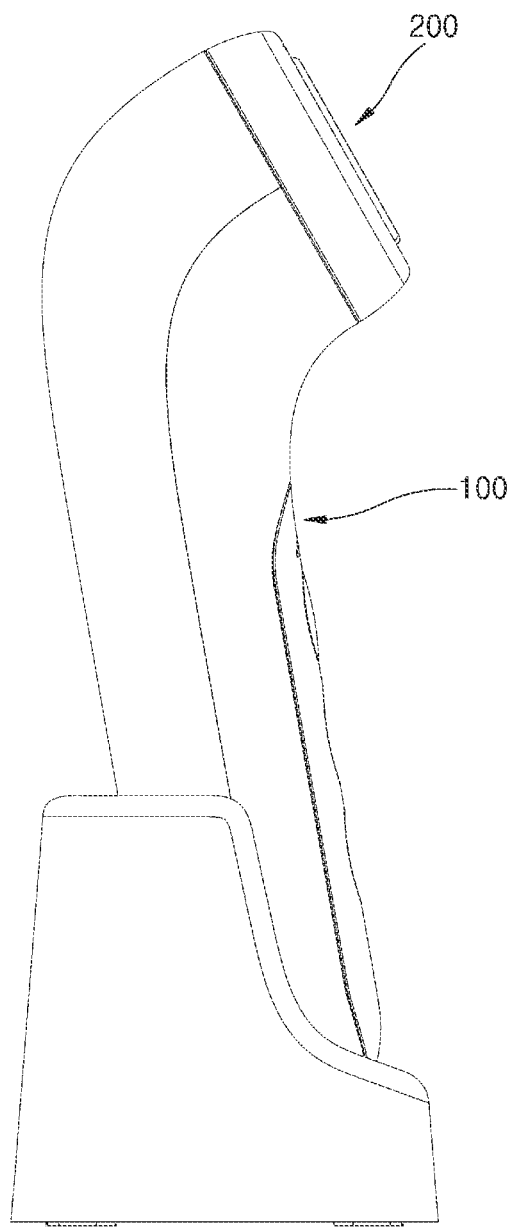
Figure 3:
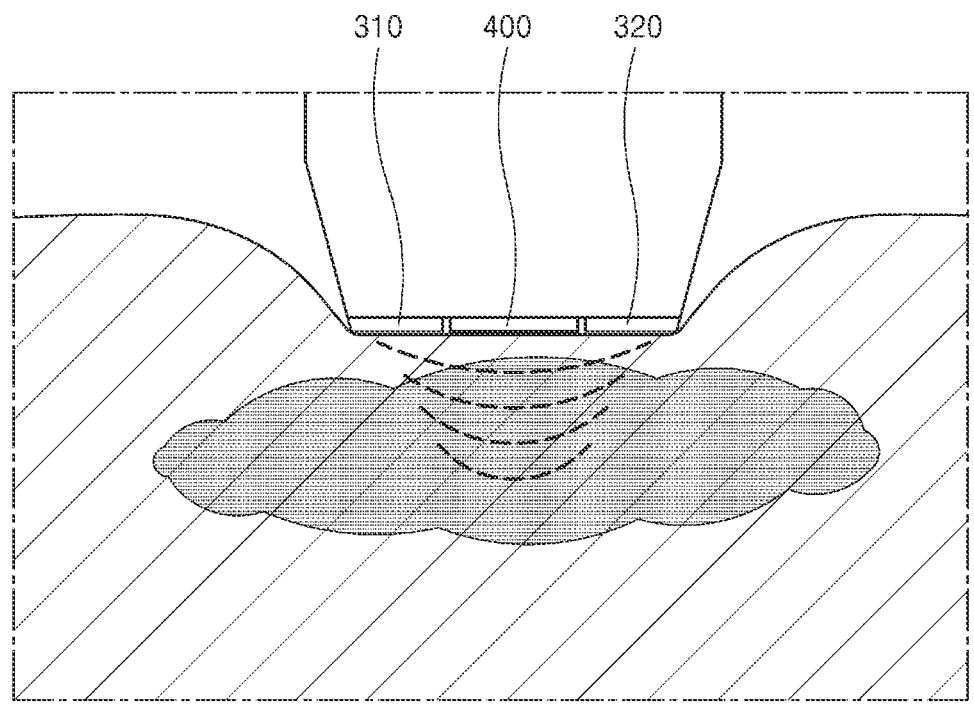
FIG. 3 is a view showing the use of a skin management device according to an embodiment of the present disclosure.

FIGS. 1 and 2 are views showing the appearance of a skin management device according to an embodiment of the present disclosure. FIG. 3 is a view showing the use of a skin management device according to an embodiment of the present disclosure.

The skin management device according to an embodiment of the present disclosure includes a main body housing 110 forming the appearance, a high-frequency generation module 120 mounted in the main body housing 110, a main body portion 100 including an ultrasound generation module 130 and a control module 140, a skin contact head 200 provided at a position of the main body portion 100 and capable of contacting user's skin, a high-frequency electrode 300 disposed in the skin contact head 200 and connected to the high-frequency generation module 120, and an ultrasound electrode 400 disposed in the skin contact head 200 and connected to the ultrasound generation module 130.

The main body portion 100 forms the appearance of the skin management device.

The main body portion 100 may have a shape and structure that enables a user may conveniently assemble and carry the skin management device according to the present disclosure, and the present disclose is not necessarily limited to the shape illustrated in the drawings.

The main body portion 100 may include the main body housing 110 forming the appearance, and the high-frequency generation module 120, the ultrasound generation module 130, and the control module 140, which are mounted in the main body housing 110.

The main body housing 110 forms the appearance of the main body portion 100. The main body housing 110 may have a shape so that a user may conveniently assemble and carry the skin management device according to the present disclosure. For example, the main body housing 110 may have a shape suitable for a user to grip with one hand.

The high-frequency generation module 120 may be mounted in the main body portion 100. The high-frequency generation module 120 may a device for outputting high-frequency energy. The high-frequency generation module 120 may emit high-frequency energy through the high-frequency electrode 300 that is described below. The high frequency generated from the high-frequency generation module 120 may have a frequency of, for example 0.1 MHz or more, but the present disclosure is not limited thereto. As a multiple of well-known technologies have been published in connection with the high-frequency generation module 120, the detailed configuration of the high-frequency generation module 120 is not limited. High frequency may increase a skin heat massage effect through heat generation, and perform a function to increase the moisturizing effect and the nourishing effect of cosmetics by allowing nourishing ingredients of the cosmetics to penetrate deep into the skin by an electroporation method.

The ultrasound generation module 130 may be mounted in the main body portion 100. The ultrasound generation module 130 outputs ultrasonic energy. The ultrasound generation module 130 may emit ultrasonic energy through the ultrasound electrode 400 that is described below. The ultrasound generated from the ultrasound generation module 130 may have a frequency of, for example, 1-7 MHz, but the present disclosure is not limited thereto. As a multiple of well-known technologies have been published in connection with the ultrasound generation module 130, the detailed configuration of the ultrasound generation module 130 is not limited. Ultrasound may provide skin beauty, such as wrinkle improvement, and obesity treatment effects, by ablating, for example, specific tissues.

The control module 140 may be mounted in the main body portion 100. The control module 140 controls the operations of the high-frequency generation module 120 and the ultrasound generation module 130. The control module 140 may include a central processing unit (CPU). The control module 140 may include a power device for providing electric power, and a processing device for controlling the operations of the high-frequency generation module 120 and the ultrasound generation module 130 according to an input signal.

The control module 140 may generate an output signal in response to a signal provided from the outside of the control module 140. For example, the control module 140 may generate an output signal in response to a user's input signal provided through an input portion 150. The output signal generated from the control module 140 may be operation signals to control the operations of the high-frequency generation module 120 and the ultrasound generation module 130.

The input portion 150 that is manipulated by a user may be provided on the outside of the main body portion 100. The input portion 150 may include a button, a display, or the like. The user's input signal may be input through the input portion 150. The input signal may be any signal for, for example, an operation ON/OFF control, an operation time control, an operation temperature control, and the like.

The skin contact head 200 includes a face provided at one end position of the main body portion 100.

The skin contact head 200 includes a portion having a size. The high-frequency electrode 300 and the ultrasound electrode 400 that are described below may be disposed in the skin contact head 200.

The high-frequency electrode 300 is an electrode disposed in the skin contact head 200.

The high-frequency electrode 300 is connected to the high-frequency generation module 120. The high-frequency electrode 300 may provide to the outside the high frequency generated from the high-frequency generation module 120. Accordingly, when the high-frequency generation module 120 is in an ON state, and the body of a user is in contact with the high-frequency electrode 300, high frequency may be provided to the user's body through the high-frequency electrode 300.

The ultrasound electrode 400 is disposed in the skin contact head 200.

The ultrasound electrode 400 is connected to the ultrasound generation module 130. The ultrasound electrode 400 may provide to the outside the ultrasound generated from the ultrasound generation module 130. Accordingly, when the ultrasound generation module 130 is in an ON state, and the user's body is in contact with the ultrasound electrode 400, ultrasound may be provided to the user's body through the ultrasound electrode 400.

The high-frequency electrode 300 and the ultrasound electrode 400 may include a single metal or alloy having conductivity as a base substrate. According to an embodiment, the high-frequency electrode 300 and the ultrasound electrode 400 may each include components that transmit a stable high frequency output to a fat layer deep in the skin without any trouble according to a contact with the skin and increase heat generation and decomposition efficiency by fat layer stimulation. Furthermore, the high-frequency electrode 300 and the ultrasound electrode 400 may each have an appropriately processed surface, for example, a coated surface or a curved surface, etc., not to damage the user's skin when touching the user's skin. Any well-known technology may be used therefor.

FIG. 3 is a view showing the use and operation of a skin management device according to an embodiment of the present disclosure.

When the skin contact head 200 contacts the user's skin, and an operation command is input through the input portion 150, the high-frequency generation module 120 and the ultrasound generation module 130 in the main body portion 100 may be operated. Accordingly, high frequency and ultrasound may be provided to the user's skin through the high-frequency electrode 300 and the ultrasound electrode 400. The high-frequency electrode 300 and the ultrasound electrode 400 may be independently and individually operated.

According to the skin management device according to an embodiment of the present disclosure, in a state in which the high-frequency generation module 120 and the ultrasound generation module 130 are simultaneously operated, when the skin contact head 200 contacts the user's skin, the high frequency generated from the high-frequency generation module 120 and the ultrasound generated from the ultrasound generation module 130 may each be simultaneously provided to the user's skin through the high-frequency electrode 300 and the ultrasound electrode 400.

Accordingly, the electric deep-heat by high frequency and the heat by ultrasound physical vibration may be simultaneously provided to the skin. Accordingly, the skin management effect may be improved.

Figure 4:
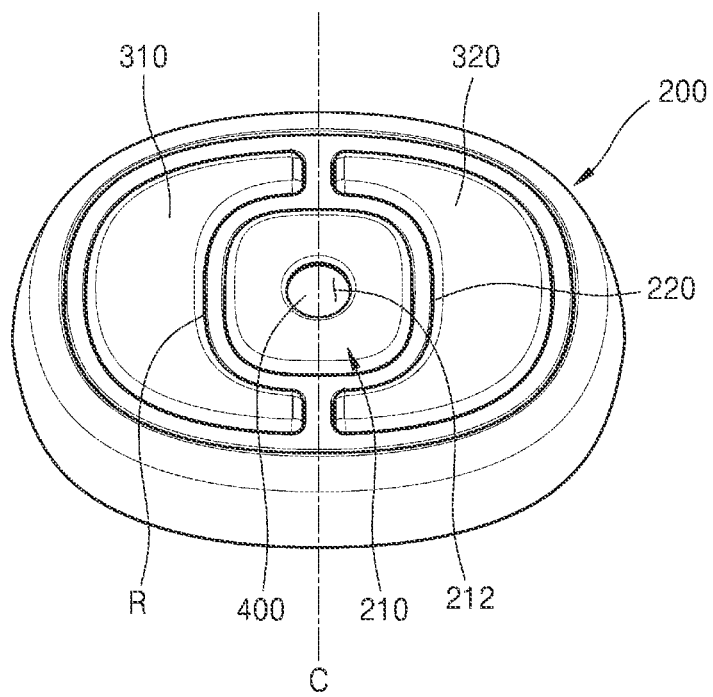
FIG. 4 is a view showing the structure of a skin contact head and a high-frequency electrode and an ultrasound electrode provided in the skin contact head.
Figure 5:
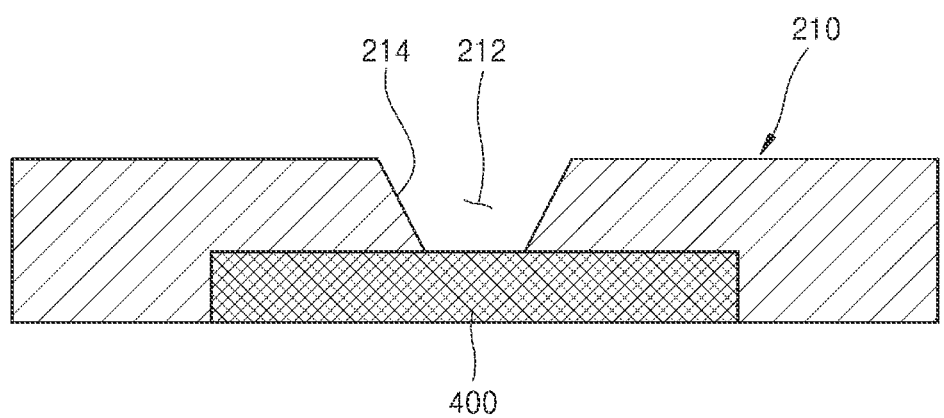
FIG. 5 is a cross-sectional view showing the structure of the skin contact head.

FIG. 4 illustrates the structures of the skin contact head 200, and the high-frequency electrode 300 and the ultrasound electrode 400 provided in the skin contact head 200, according to an embodiment. FIG. 5 is a cross-sectional view showing the structure of the skin contact head 200.

In the following description, the detailed configurations of the high-frequency electrode 300 and the ultrasound electrode 400 according to an embodiment are described.

According to an embodiment, the high-frequency electrode 300 includes a positive pole portion 310 and a negative pole portion 320, which are apart from each other, and the high-frequency electrode 300 may be a bipolar RF electrode in which a current is conducted between the positive pole portion 310 and the negative pole portion 320. Accordingly, the high-frequency electrode 300 may include the positive pole portion 310 and the negative pole portion 320. The positive pole portion 310 and the negative pole portion 320 may be disposed apart a distance from each other.

In addition, the ultrasound electrode 400 may be disposed between the positive pole portion 310 and the negative pole portion 320 of the high-frequency electrode 300.

As the high-frequency electrode 300 and the ultrasound electrode 400 are arranged as above, high frequency and ultrasound may be simultaneously and effectively provided to a specific position on the skin.

In other words, in a state in which the user's body contacts the skin contact head 200, when the high-frequency generation module 120 and the ultrasound generation module 130 are operated, a high-frequency current is conducted through a body portion located between the positive pole portion 310 and the negative pole portion 320 of the high-frequency electrode 300. Simultaneously, the body portion may receive ultrasound because the body portion is located under the ultrasound electrode 400. Accordingly, skin management effect may be improved.

According to an embodiment, the positive pole portion 310 and the negative pole portion 320 may each have a crescent shape having a sunken surface R that his sunken to one side. In addition, the positive pole portion 310 and the negative pole portion 320 may be disposed at both side portions of the skin contact head 200. In this state, the positive pole portion 310 and the negative pole portion 320 may be disposed such that the sunken surfaces R face each other.

In addition, the ultrasound electrode 400 may be disposed at the center of the skin contact head 200 and between the positive pole portion 310 and the negative pole portion 320 of the high-frequency electrode 300, in particular, between the sunken surface R of the positive pole portion 310 and the sunken surface R of the negative pole portion 320.

As the high-frequency electrode 300 and the ultrasound electrode 400 have the shape and arrangement described above, high frequency and ultrasound may be simultaneously and effectively provided to a specific position on the skin. In other words, the high frequency generated from the positive pole portion 310 is transmitted to the negative pole portion 320 by passing through the skin. Simultaneously, the ultrasound by the ultrasound electrode 400 is provided to the inside of the skin along the path through which the current passes. In particular, as the sunken surface R of the positive pole portion 310 and the sunken surface R of the negative pole portion 320 face each other, and the ultrasound electrode 400 is disposed between the sunken surfaces R, the high-frequency electrode 300 surrounds entirely the ultrasound electrode 400. Accordingly, high frequency and ultrasound may be intensively provided to a specific portion of the body disposed below the ultrasound electrode 400. In other words, according to an embodiment, high frequency and ultrasound may be intensively provided to a specific position on the skin along the path of high frequency and ultrasound implemented according to the shape and arrangement structure of the high-frequency electrode 300 and the ultrasound electrode 400. Accordingly, skin management effect may be improved.

According to an embodiment, the skin contact head 200 may include a cover member 210 that covers at least a part of the ultrasound electrode 400.

For example, the ultrasound electrode 400 may be fixed at one position of the skin contact head 200, and the cover member 210 covering the ultrasound electrode 400 may be fixed on the skin contact head 200. For example, the skin contact head 200 may have a structure in which an insertion portion 220 having a hole is provided and the ultrasound electrode 400 is disposed in the insertion portion 220 so that the ultrasound electrode 400 is exposed through a space in the insertion portion 220, and the skin contact head 200 is inserted in the insertion portion 220 and fixed thereon.

According to an embodiment, the cover member 210 may include a window hole 212 that covers the ultrasound electrode 400 and exposes at least a part of the ultrasound electrode 400. The ultrasound provided by the ultrasound electrode 400 may be transmitted to the user's body through the window hole 212.

An in the embodiment, as the cover member 210 covering the ultrasound electrode 400 is provided, the area and strength of the ultrasound provided by the ultrasound electrode 400 may be appropriately adjusted.

In addition, according to an embodiment, the area of the window hole 212 may optionally vary by substituting the cover member 210. In this case, the area and strength of the ultrasound provided by the ultrasound electrode 400 may be appropriately adjusted.

FIG. 5 is a cross-sectional view showing a portion of the ultrasound electrode 400 covered by the cover member 210. As illustrated in FIG. 5, according to an embodiment of the present disclosure, the cover member 210 may have a thickness, and the window hole 212 may have a depth. In addition, an inner circumferential surface of the window hole 212 is configured as a slope surface 214 and the cross-sectional area of the window hole 212 may increase toward the outside.

According to the present embodiment, the inner circumferential surface of the window hole 212 may be configured as an inclined surface. Accordingly, when the skin management device according to the present disclosure is used in a state in which gel is applied to the skin, accumulation of the gel applied to the skin in the window hole 212 may be effectively reduced. In addition, even when the gel is accumulate in the window hole 212, the gel may be removed from the window hole 212 by simply cleaning the same. Accordingly, user convenience and hygiene may be improved.

When, as described above, the inner circumferential surface of the window hole 212 is not an inclined surface, when the skin management device is used in a state in which gel is applied to the skin, the gel may be easily accumulate in the window hole 212 and cleaning the accumulated gel is difficult. In this case, even when cleaning the gel by using a tool such as a cotton swab and the like, the gel sticks at the corner, and thus, it is difficult to easily clean and remove the gel.

In contrast, in the skin management device according to an embodiment of the present disclosure, as in the embodiment above, the inner circumferential surface of the window hole 212 is configured as an inclined surface, and thus, the accumulation of gel in the window hole 212 may be prevented, and even when the gel is accumulated in the window hole 212, the gel may be simply cleaned and removed from the window hole 212.

In particular, like the skin management device of the present disclosure, for a skin management device using ultrasound and high frequency, it is frequent to apply gel (conductive gel) to user's skin before use. Accordingly, when gel cleaning convenience is improved, user convenience and hygiene may be greatly improved.

Figure 6:
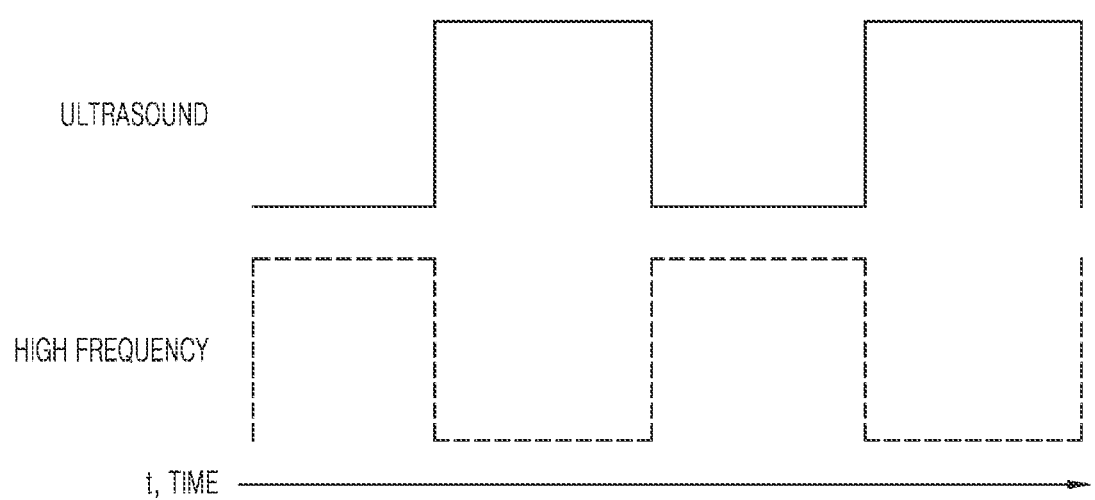
FIGS. 6 and 7 are waveform diagrams of ultrasound and high frequency generated during the operation of a skin management device according to an embodiment of the present disclosure.
Figure 7:
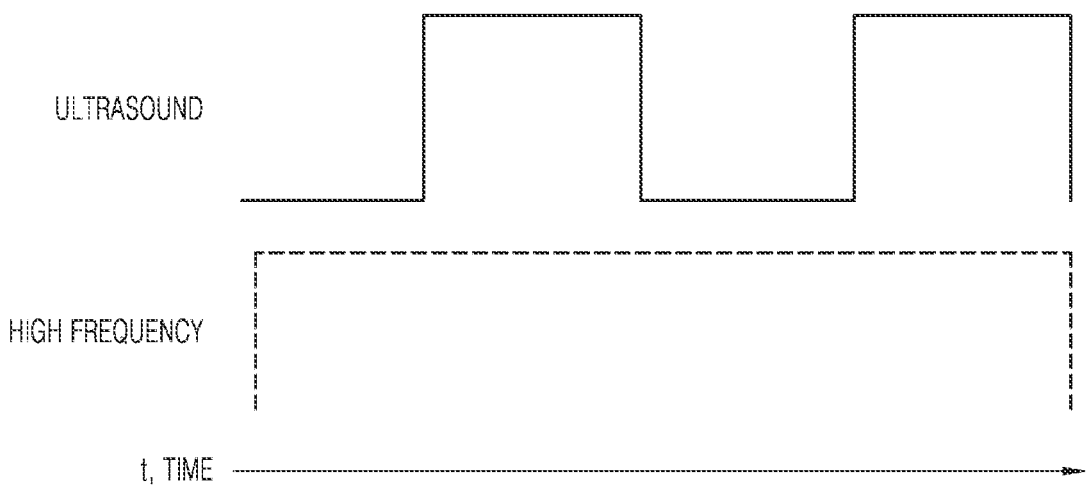

FIGS. 6 and 7 are waveform diagrams of ultrasound and high frequency generated during the operation of a skin management device according to an embodiment of the present disclosure.

The skin management device according to an embodiment of the present disclosure may have an operation mode. The operation mode may be controlled and commanded by a control module 140. The operation mode may be selected by an input signal input by a user through the input portion 150.

For example, the operation mode by the control module 140 may include a first operation mode as illustrated in FIG. 6. In the first operation mode, the high-frequency generation module 120 and the ultrasound generation module 130 are alternately operated. Accordingly, as illustrated in FIG. 6, when ultrasound is generated, high frequency is not generated, and when high frequency is generated, ultrasound is not generated. In other words, turning ON/OFF of ultrasound by the ultrasound generation module 130 and turning ON/OFF of high frequency by the high-frequency generation module 120 may alternate with each other.

In another example, the operation mode by the control module 140 may include a second operation mode as illustrated in FIG. 7. In the second operation mode, any one of the high-frequency generation module 120 and the ultrasound generation module 130 operates discontinuously. For example, as illustrated in FIG. 7, while high frequency is continuously output, ultrasound is alternately output by repeating turning ON and OFF. Reversely, it is possible that, while ultrasound is continuously output, high frequency is alternately output by repeating turning ON and OFF.

Figure 8:
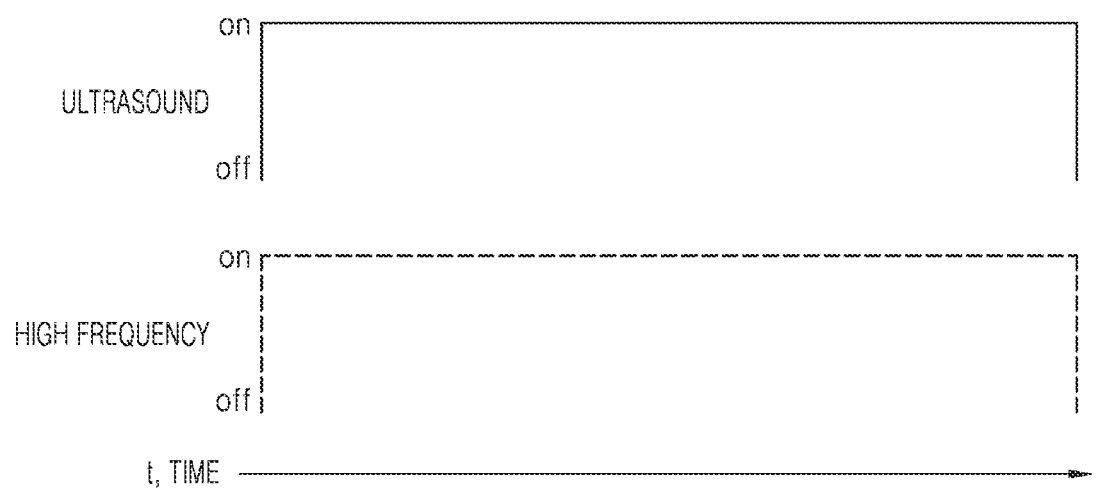
FIG. 8 is a waveform diagram of ultrasound and high frequency generated during the operation of a skin management device according to the related art.

FIG. 8 is a waveform diagram of ultrasound and high frequency generated during the operation of a skin management device according to the related art. Unlike the present disclosure, in the skin management device according to the related art, ultrasound and high frequency are continuously provided.

Although both of high frequency and ultrasound may provide heat to the skin, there is a difference in the actual feeling. While high frequency provides a sense of heat that slowly increases, ultrasound provides heat with slight stinging pain. The skin management device according to an embodiment of the present disclosure does not simultaneously and continuously provide ultrasound and high frequency, and may have an operation mode in which at least one of ultrasound and high frequency is discontinuously provided. According to an embodiment, the skin management device according to an embodiment of the present disclosure may have an operation mode in which ultrasound and high frequency are alternately provided. Accordingly, in the skin management device according to an embodiment of the present disclosure, occurrence of user's pain due to simultaneously provision of ultrasound and high frequency may be reduced, and user convenience may be improved.

Figure 9:
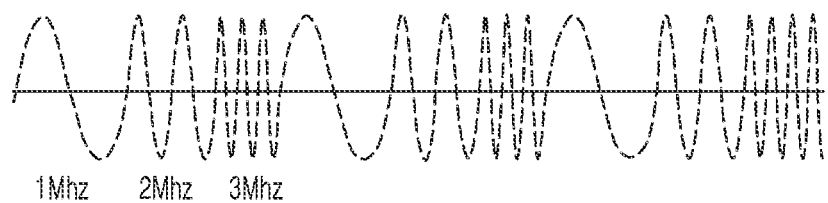
FIG. 9 is a waveform diagram of ultrasound and high frequency generated during the operation of a skin management device according to an embodiment of the present disclosure.
Figure 9:
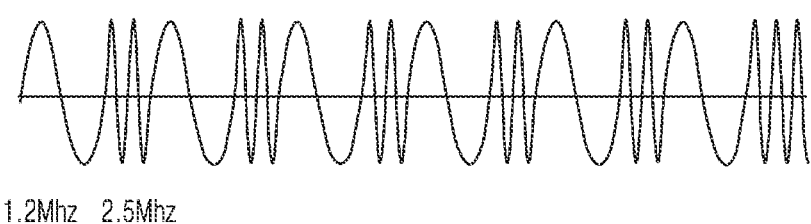

FIG. 9 is a waveform diagram of ultrasound and high frequency generated during the operation of a skin management device according to an embodiment of the present disclosure.

As described above, the skin management device according to an embodiment of the present disclosure may have an operation mode. The operation mode may be controlled and commanded by the control module 140.

For example, an operation by the control module 140 may include a third operation mode as illustrated above in FIG. 9. In the third operation mode, the frequency of high frequency provided by the high-frequency generation module 120 is variable. For example, 1 MHZ, 2 MHZ, and 3 MHz may be periodically repeated as the frequency of high frequency. However, the disclosure is not limited thereto.

In another example, the operation mode by the control module 140 may include a fourth operation mode as illustrated below in FIG. 9. In the fourth operation mode, the frequency of ultrasound provided by the ultrasound generation module 130 is variable. For example, 1.2 MHz and 2.5 MHz may be periodically repeated as the frequency of ultrasound. However, the disclosure is not limited thereto.

In addition, although not illustrated, the first to fourth operation modes may be mixed. In other words, it is possible that, while at least one of the high-frequency generation module 120 and the ultrasound generation module 130 operates by repeating turning ON/OFF, the frequency of at least one of high frequency and ultrasound that are provided may vary. For example, it is possible that, while the high-frequency generation module 120 operates in an ON/OFF pattern, the frequency of high frequency provided by the high-frequency generation module 120 may vary. Simultaneously, the frequency of ultrasound provided by the ultrasound generation module 130 may vary.

Figure 10:
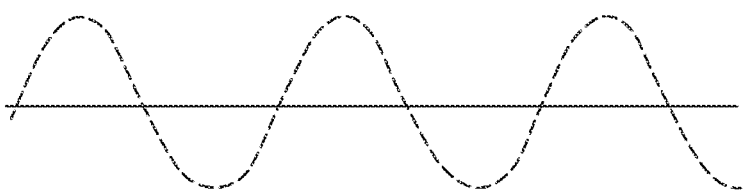
FIG. 10 is a waveform diagram of ultrasound and high frequency generated during the operation of a skin management device according to the related art.
Figure 10:
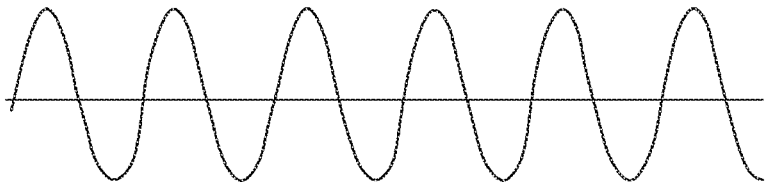

FIG. 10 is a waveform diagram of ultrasound and high frequency generated during the operation of a skin management device according to the related art. In the skin management device according to the related art, in an operation process, ultrasound and high frequency are provided in the form of constant waveform and frequency.

The high frequency and ultrasound vibrate cells with electrical energy to be converted into thermal energy, and an infiltration depth in the skin may vary depending on the frequency range of high frequency and ultrasound. According to an embodiment of the present disclosure, the frequencies of high frequency and ultrasound vary, and high frequency and ultrasound having variable frequencies are provided to the skin in a mixed form, and thus, the form of vibration is diversified, and more effective skin improvement effect may be achieved.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A skin management device comprising:
a main body portion having a hand piece structure and including a high-frequency generation module for generating a high frequency current, an ultrasound generation module for generating ultrasound, and a control module, which are mounted on the main body portion;
a skin contact head provided at one position of the main body portion to be capable of contacting user's skin;
a high-frequency electrode disposed in the skin contact head and connected to the high-frequency generation module; and
an ultrasound electrode disposed in the skin contact head and connected to the ultrasound generation module,
wherein the high-frequency generation module is an energy output device that outputs high frequency energy through the high-frequency electrode,
the ultrasound generation module is an energy output device that outputs ultrasound vibrations through the ultrasound electrode,
the high-frequency electrode comprises a bipolar RF electrode including a positive pole portion and a negative pole portion, which are apart from each other,
each of the positive pole portion and the negative pole portion has a crescent shape having a sunken surface,
the positive pole portion and the negative pole portion are disposed at both side portions of the skin contact head, with the sunken surfaces facing each other,
the ultrasound electrode is disposed at a center of the skin contact head between the sunken surfaces of the positive pole portion and the negative pole portion,
the high-frequency current is a high-frequency current of 0.1 Mhz or more generated between the positive pole portion and the negative pole portion,
the high-frequency current generates electric deep-heat in the user's skin in contact with the high-frequency electrode, and
during simultaneous operations of the high-frequency generation module and the ultrasound generation module, when the high-frequency electrode and the ultrasound electrode disposed in the skin contact head contact the user's skin, high frequency current and ultrasound are simultaneously provided to the user's skin.

2. The skin management device of claim 1, wherein the skin contact head comprises a cover member covering at least a part of the ultrasound electrode.

3. The skin management device of claim 2, wherein the cover member includes a window hole that exposes the ultrasound electrode.

4. The skin management device of claim 3, wherein an area of the window hole optionally varies.

5. The skin management device of claim 3, wherein the cover member has a thickness, the window hole has a depth, an inner circumferential portion of the window hole has a slope surface, and a cross-sectional area of the window hole increases toward outside.

6. The skin management device of claim 1, wherein the control module has a first operation mode in which the high-frequency generation module and the ultrasound generation module alternately operate.

7. The skin management device of claim 1, wherein the control module has a second operation mode in which at least one of the high-frequency generation module and the ultrasound generation module discontinuously operates.

8. The skin management device of claim 1, wherein the control module has a third operation mode in which a frequency of high frequency generated by the high-frequency generation module varies.

9. The skin management device of claim 1, wherein the control module has a fourth operation mode in which a frequency of ultrasound generated by the ultrasound generation module varies.

* * * * *